United States Patent
Tanaka

(10) Patent No.: US 12,139,121 B2
(45) Date of Patent: Nov. 12, 2024

(54) VEHICLE CONTROL DEVICE, VEHICLE CONTROL METHOD, AND COMPUTER-READABLE RECORDING MEDIUM HAVING STORED THEREON VEHICLE CONTROL PROGRAM

(71) Applicant: Daimler AG, Stuttgart (DE)

(72) Inventor: Tsuyoshi Tanaka, Kanagawa (JP)

(73) Assignee: Daimler Truck AG, Leinfelden-Echterdingen (DE)

( * ) Notice: Subject to any disclaimer, the term of this patent is extended or adjusted under 35 U.S.C. 154(b) by 182 days.

(21) Appl. No.: 17/781,668

(22) PCT Filed: Oct. 22, 2020

(86) PCT No.: PCT/JP2020/039667
§ 371 (c)(1),
(2) Date: Jun. 1, 2022

(87) PCT Pub. No.: WO2021/111755
PCT Pub. Date: Jun. 10, 2021

(65) Prior Publication Data
US 2023/0001893 A1    Jan. 5, 2023

(30) Foreign Application Priority Data
Dec. 2, 2019    (JP) .................................. 2019-217976

(51) Int. Cl.
*B60T 7/22* (2006.01)
*B60T 7/14* (2006.01)
(Continued)

(52) U.S. Cl.
CPC  *B60T 7/22* (2013.01); *B60T 7/14* (2013.01); *B60T 2201/022* (2013.01); *B60T 2210/30* (2013.01); *B60T 2220/00* (2013.01)

(58) Field of Classification Search
CPC ........ B60T 7/22; B60T 7/14; B60T 2201/022; B60T 2210/30; B60T 2220/00;
(Continued)

(56) References Cited

U.S. PATENT DOCUMENTS 6,691,015 B1 *  2/2004  Levine ..................... G08G 1/22
                                                   340/905
7,774,137 B2 *  8/2010  Thorne .................. G08G 1/162
                                                    701/96
(Continued)

FOREIGN PATENT DOCUMENTS

CN    1862227 A    11/2006
EP    1 721 800 A2    11/2006
(Continued)

OTHER PUBLICATIONS

PCT/JP2020/039667, English translation of Written Opinion of the International Searching Authority (PCT/ISA/237) dated Nov. 24, 2020 (Four (4) pages).
(Continued)

*Primary Examiner* — Jaime Figueroa
(74) *Attorney, Agent, or Firm* — Crowell & Moring LLP

(57) ABSTRACT

A vehicle control device includes a first control unit that executes, when an abnormality of a driver of a vehicle is detected, stop control, a second control unit that executes, when the vehicle is determined to have a risk of collision, deceleration control, a determination unit that identifies an object around the vehicle as a target candidate of the collision and determines whether or not there is the risk of the collision with the identified target candidate, and a setting unit that sets, when the abnormality is detected, an operation mode of the deceleration control to a special mode from a normal mode, the normal mode provided for cases in which the abnormality is undetected. The determination unit expands a range for identifying the object around the vehicle
(Continued)

as the target candidate of the collision in the special mode as compared with the range in the normal mode.

9 Claims, 12 Drawing Sheets

(51) Int. Cl.
*B60T 17/18* (2006.01)
*B60W 10/18* (2012.01)
*B60W 30/09* (2012.01)

(58) Field of Classification Search
CPC ....... B60T 17/18; A61B 5/0205; A61B 5/021; A61B 5/024; A61B 5/318; A61B 5/6893; B60W 2040/0818; B60W 10/18; B60W 30/09; B60W 30/0956; B60W 50/14
See application file for complete search history.

(56) References Cited

U.S. PATENT DOCUMENTS

| | | | | |
|---|---|---|---|---|
| 8,698,639 | B2* | 4/2014 | Fung | B60W 10/30 340/576 |
| 9,047,780 | B2* | 6/2015 | Guarnizo Martinez | G08G 1/168 |
| 9,090,234 | B2* | 7/2015 | Johnson | B60T 7/22 |
| 9,292,471 | B2* | 3/2016 | Fung | B62D 6/001 |
| 9,751,534 | B2* | 9/2017 | Fung | G06V 10/764 |
| 9,884,628 | B1* | 2/2018 | Grant | B60W 40/08 |
| 10,252,725 | B2* | 4/2019 | Numazawa | B60W 50/10 |
| 10,525,979 | B1* | 1/2020 | Grant | B60W 40/08 |
| 11,513,516 | B2* | 11/2022 | Taguchi | G05D 1/24 |
| 2002/0091479 | A1* | 7/2002 | Maruko | B60T 7/22 701/96 |
| 2007/0021876 | A1 | 1/2007 | Isaji et al. | |
| 2007/0168129 | A1* | 7/2007 | Thorne | B60Q 1/535 701/96 |
| 2009/0128318 | A1* | 5/2009 | Nagata | B60T 7/22 340/467 |
| 2010/0253526 | A1* | 10/2010 | Szczerba | G08B 21/06 340/576 |
| 2012/0062743 | A1* | 3/2012 | Lynam | G05D 1/0061 348/148 |
| 2013/0226408 | A1* | 8/2013 | Fung | G08G 1/166 701/1 |
| 2013/0311043 | A1* | 11/2013 | Kobana | B62D 15/025 701/41 |
| 2014/0046567 | A1* | 2/2014 | Schuler | B60W 10/184 701/70 |
| 2014/0142798 | A1* | 5/2014 | Guarnizo Martinez | B60W 10/18 701/23 |
| 2014/0156157 | A1* | 6/2014 | Johnson | B60T 7/22 701/70 |
| 2015/0006012 | A1* | 1/2015 | Kammel | B60W 30/06 701/23 |
| 2015/0166059 | A1* | 6/2015 | Ko | B60W 30/09 701/28 |
| 2015/0183441 | A1* | 7/2015 | Aoki | B60W 40/09 434/62 |
| 2015/0329091 | A1* | 11/2015 | Johnson | B60T 7/22 701/70 |
| 2016/0001781 | A1* | 1/2016 | Fung | G07C 9/37 701/36 |
| 2016/0031479 | A1* | 2/2016 | Fung | B60K 28/066 701/42 |
| 2017/0101107 | A1* | 4/2017 | Milch | B60W 40/09 |
| 2017/0113694 | A1* | 4/2017 | Nakatsuka | G08G 1/167 |
| 2017/0158054 | A1* | 6/2017 | Munaoka | B60Q 5/005 |
| 2017/0193384 | A1* | 7/2017 | Mudalige | G08G 1/161 |
| 2017/0267255 | A1* | 9/2017 | Numazawa | B60W 50/082 |
| 2019/0077401 | A1* | 3/2019 | Katagiri | B60W 10/18 |
| 2019/0135291 | A1* | 5/2019 | Sim | A61B 5/163 |
| 2019/0137999 | A1* | 5/2019 | Taguchi | G08G 1/165 |
| 2020/0283028 | A1* | 9/2020 | Oba | B60W 60/0057 |
| 2021/0016805 | A1* | 1/2021 | Oba | A61B 5/18 |

FOREIGN PATENT DOCUMENTS

| | | |
|---|---|---|
| JP | 2007-331652 A | 12/2007 |
| JP | 2010-143578 A | 7/2010 |
| JP | 2019-182012 A | 10/2019 |
| KR | 10-2006-0117244 A | 11/2006 |

OTHER PUBLICATIONS

English-language Extended European Search Report issued in European application No. 20895736.5-1012 dated May 3, 2023 (Five (5) pages).
PCT/JP2020/039667, International Search Report dated Nov. 24, 2020 (Two (2) pages).

* cited by examiner

VEHICLE CONTROL DEVICE, VEHICLE CONTROL METHOD, AND COMPUTER-READABLE RECORDING MEDIUM HAVING STORED THEREON VEHICLE CONTROL PROGRAM

FIELD

The present invention relates to a vehicle control device, a vehicle control method, and a vehicle control program which automatically decelerate a vehicle.

BACKGROUND

Conventionally, a collision damage mitigation brake (AEBS; Advanced Emergency Braking System) has been known, which automatically decelerates a vehicle when the vehicle is likely to collide with another vehicle or with an obstacle in front of the vehicle. In recent years, development has been in progress also for a driver abnormality response system (EDSS; Emergency Driving Stop System) which automatically decelerates and then stops a vehicle when an abnormality such as fainting of a driver is detected (see Patent Document 1 for example).

CITATION LIST

Patent Document

Patent Document 1: Japanese Laid-open Patent Publication No. 2007-331652

SUMMARY

Problems to be Solved

During the activation of the driver abnormality response system described above, since the driver has a high risk of not being able to drive, it is important to activate the collision damage mitigation brake more appropriately to avoid collision of the vehicle. However, since in general, the collision damage mitigation brake is based on the premise that the driver has no abnormality, and also has a risk when having caused unnecessary deceleration of the vehicle due to erroneous activation, the situations for activating the collision damage mitigation brake are limited. Thus, there has been a demand for a technique that more reliably avoids collision when a driver has an abnormality.

The present disclosure has been devised in view of such problems, and an object thereof is to more reliably reduce a risk of collision when an abnormality of a driver is detected.

Means to Solve the Problem

The present disclosure has been made to solve at least a part of the above-mentioned problems, and can be realized as following aspects or application examples.

(1) A vehicle control device according to this present application example includes: a first control unit that executes, when an abnormality of a driver of a vehicle is detected, stop control which automatically decelerates and then stops the vehicle; a second control unit that executes, when the vehicle is determined to have a risk of collision, deceleration control which automatically decelerates the vehicle; a determination unit that identifies an object around the vehicle as a target candidate of the collision and determines whether or not there is the risk of the collision with the identified target candidate; and a setting unit that sets, when the abnormality is detected, an operation mode of the deceleration control to a special mode from a normal mode. The normal mode is provided for cases in which the abnormality is undetected. In the vehicle control device, the determination unit expands a range for identifying the object around the vehicle as the target candidate of the collision in the special mode as compared with the range in the normal mode.

Accordingly, in the special mode, the range of the target candidate is expanded to result in a higher probability of determining that there is the risk of the collision with the target candidate as compared with the probability in the normal mode, so that the opportunity to execute the deceleration control increases. Therefore, when the abnormality of the driver is detected, the deceleration control is more likely to be executed as compared with cases where the abnormality of the deriver is undetected. Hence, even if the driver is in a state unable to drive, the collision can be easily avoided.

On the other hand, when the abnormality of the driver is undetected, the target candidate is narrowed to result in a lower probability of determining that there is the risk of the collision as compared with the case where the abnormality of the driver is detected. Accordingly, when the driver has no abnormality and has a high possibility of being able to avoid the collision by one's driving operation, erroneous activation of the deceleration control (unnecessary execution of the deceleration control) are reduced, so that unnecessary deceleration of the vehicle due to the deceleration control can be easily avoided.

(2) In the vehicle control device according to the present application example, the determination unit may identify the object that has been continuously detected for a predetermined first period or longer as the target candidate in the normal mode, and may identify the object that has been continuously detected for a predetermined second period or longer as the target candidate in the special mode. The predetermined second period may be shorter than the predetermined first period.

In the special mode, by regarding the object which has been continuously detected for a shorter duration (detection period) as the target candidate, the target candidate is identified earlier than in the normal mode. As a result, in the special mode, even if the target is detected late, the deceleration control is started at an earlier timing as compared with the timing in the normal mode, so that the collision of the vehicle is easily avoided at a higher probability.

On the other hand, in the normal mode, by regarding the object which has been continuously detected for a longer duration (detection period) as the target candidate, the target candidate is identified more accurately than in the special mode. As a result, in the normal mode, the accuracy of determining presence or absence of a collision risk is enhanced, which further reduces erroneous activation of the deceleration control.

(3) In the vehicle control device according to the present application example, the determination unit may preferentially regard the object of a predetermined type as the target candidate in the normal mode, and may identify the target candidate regardless of the predetermined type in the special mode.

In the special mode, by allowing any types of objects to be the target candidate, the deceleration control is executed when there is the risk of the collision with any types of objects. Accordingly, the collision of the vehicle is more easily avoided in the special mode.

On the other hand, in the normal mode, by preferentially regarding the object of the predetermined type as the target candidate, the execution of the deceleration control is avoided for the object such as the one detected based on unreliable information or the one with a structure (shape) that is less likely to cause damage even in collision. Therefore, in the normal mode, unnecessary deceleration of the vehicle due to the deceleration control is further suppressed.

(4) In the vehicle control device according to the present application example, the determination unit may exclude the object within a predetermined range from the target candidate in the normal mode, and may identify the target candidate regardless of the predetermined range in the special mode.

In the special mode, by allowing the object located in any directions to be the target candidate, the deceleration control is executed when there is the risk of the collision with the object located in any directions. Accordingly, the collision of the vehicle is more easily avoided in the special mode.

On the other hand, in the normal mode, by excluding the object within the predetermined range from the target candidate, the execution of the deceleration control is avoided for the object beside or behind the vehicle, for example. Therefore, in the normal mode, unnecessary deceleration of the vehicle due to the deceleration control is further suppressed.

(5) In the vehicle control device according to the present application example, the determination unit may exclude the object outside a traveling lane of the vehicle from the target candidate in the normal mode, and may identify the target candidate based on a traveling direction of the vehicle regardless of the traveling lane in the special mode.

In the special mode, by allowing the object outside the traveling lane but in the forward direction to be the target candidate, the deceleration control is executed when there is the risk of the collision with the object in the forward direction. Accordingly, the collision of the vehicle is more easily avoided in the special mode.

On the other hand, in the normal mode, by excluding the object outside the traveling lane of the vehicle from the target candidate, the execution of the deceleration control is avoided for another vehicle traveling in an adjacent lane, for example. Therefore, in the normal mode, unnecessary deceleration of the vehicle due to the deceleration control is further suppressed.

(6) In the vehicle control device according to the present application example, the second control unit may interrupt the executed deceleration control when the vehicle is determined to have no risk of the collision in the normal mode, and may continue the executed deceleration control even when the vehicle is determined to have no risk of the collision in the special mode.

In the special mode, even if it is determined that there is no risk of the collision, by continuing the ongoing deceleration control, the collision of the vehicle is more easily avoided.

On the other hand, in the normal mode, by interrupting the ongoing deceleration control when it is determined that there is no risk of the collision, unnecessary deceleration of the vehicle due to the deceleration control is further suppressed.

(7) In the vehicle control device according to the present application example, the second control unit may discontinue the deceleration control when a predetermined cancel operation by the driver is performed at least once in the normal mode, and may discontinue the deceleration control when the cancel operation is performed a plurality of times in the special mode.

As such, by setting the number of the cancel operations required for discontinuing the deceleration control larger in the special mode than in the normal mode, discontinuation of the deceleration control due to an unintended cancel operation is suppressed.

On the other hand, in the normal mode, by discontinuing the deceleration control even with a single cancel operation, the deceleration control can be easily discontinued when the driver determines that the deceleration control is unnecessary.

(8) A vehicle control method according to this application example includes: a first control step that executes, when an abnormality of a driver of a vehicle is detected, stop control which automatically decelerates and then stops the vehicle; a second control step that executes, when the vehicle is determined to have a risk of collision, deceleration control which automatically decelerates the vehicle; a determination step that identifies an object around the vehicle as a target candidate of the collision and determines whether or not there is the risk of the collision with the identified target candidate; and a setting step that sets, when the abnormality is detected, an operation mode of the deceleration control to a special mode from a normal mode. The normal mode is provided for cases in which the abnormality is undetected. In the vehicle control method, the determination step expands a range for identifying the object around the vehicle as the target candidate of the collision in the special mode as compared with the range in the normal mode.

This yields the same actions and effects as those of the above (1).

(9) A vehicle control program according to this application example is for causing a computer to execute a process including: a first control step that executes, when an abnormality of a driver of a vehicle is detected, stop control which automatically decelerates and then stops the vehicle; a second control step that executes, when the vehicle is determined to have a risk of collision, deceleration control which automatically decelerates the vehicle; a determination step that identifies an object around the vehicle as a target candidate of the collision and determines whether or not there is the risk of the collision with the identified target candidate; and a setting step that sets, when the abnormality is detected, an operation mode of the deceleration control to a special mode from a normal mode. The normal mode is provided for cases in which the abnormality is undetected. In the process, the determination step expands a range for identifying the object around the vehicle as the target candidate of the collision in the special mode as compared with the range in the normal mode.

This yields the same actions and effects as those of the above (1).

Effects of Invention

According to the present disclosure, when an abnormality of a driver is detected, a risk of collision can be more reliably reduced.

DESCRIPTION OF EMBODIMENT(S)

A vehicle control device, a vehicle control method, and a vehicle control program according to an embodiment will now be described with reference to the drawings. The embodiment described below is merely an example, and there is no intention to exclude application of various modifications and techniques not specified in the following embodiment. Each configuration of the present embodiment can be variously modified and implemented without departing from the gist thereof. In addition, it can be selected as needed or can be combined as appropriate.

1. Device Configuration

Figure 1:
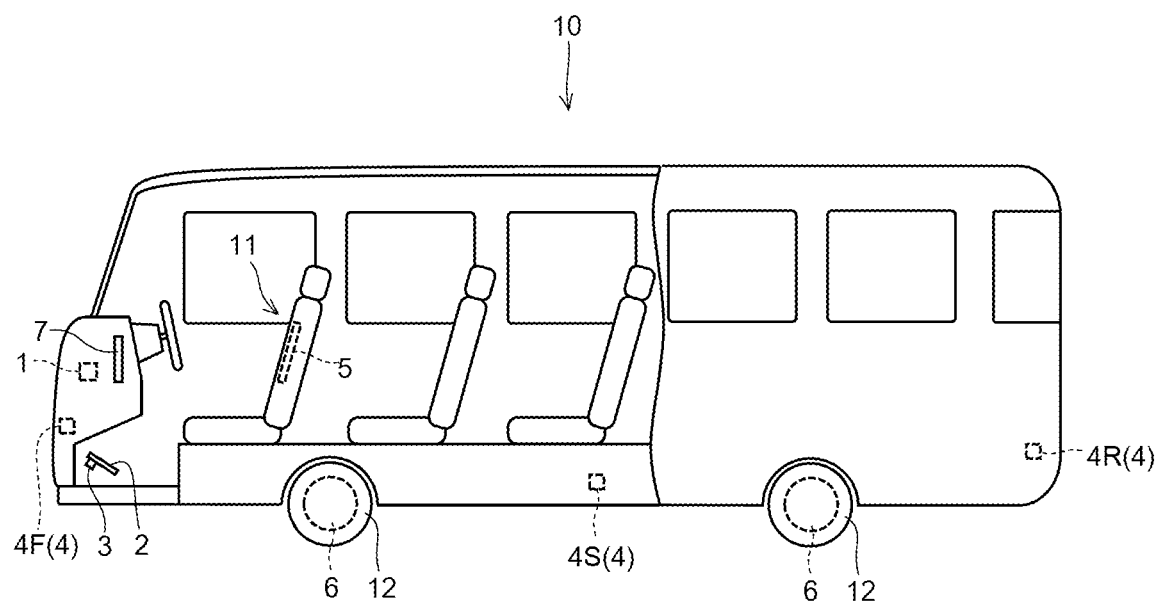
FIG. 1 is a schematic diagram of a vehicle to which a vehicle control device according to an embodiment is applied.

A vehicle control device 1 (hereinafter referred to as "control device 1") according to the present embodiment is applied to a vehicle 10 illustrated in FIG. 1. The vehicle 10 is equipped with both a so-called collision damage mitigation brake (AEBS) and a driver abnormality response system (EDSS). The collision damage mitigation brake is a function that automatically decelerates the vehicle 10 when the vehicle 10 has a risk of collision (hereinafter, abbreviated as "collision risk"). The driver abnormality response system is a function that automatically decelerates (brakes) and then stops the vehicle 10 when an abnormality such as fainting has happened to a driver of the vehicle 10. The control device 1 has functions of both the collision damage mitigation brake and the driver abnormality response system. Hereinafter, the term "deceleration control" is also used to describe the control that automatically decelerates the vehicle 10 in the collision damage mitigation brake. In addition, the term "stop control" is also used to describe the control that automatically decelerates and then stops the vehicle 10 in the driver abnormality response system. Although a bus is illustrated as the vehicle 10 in FIG. 1, the type of the vehicle 10 is not particularly limited.

The vehicle 10 is provided with an accelerator pedal 2 that the driver depresses to accelerate the vehicle 10 and an accelerator position sensor 3 that detects the amount of depression (accelerator position) AP of the accelerator pedal 2. The accelerator position AP detected by the accelerator position sensor 3 is transmitted to the control device 1.

Further, the vehicle 10 is provided with an obtaining device 4 that acquires various information about objects around the vehicle 10 and a biological sensor 5 that acquires biological information (heart rate, pulse rate, blood pressure, pulse pressure, electrocardiogram pattern, etc.) of the driver of the vehicle 10. The obtaining device 4 and the biological sensor 5 also transmit the acquired information to the control device 1.

The obtaining device 4 is configured by, for example, a camera, a radar, a combination thereof, or the like. Here, the obtaining device 4 is exemplified by a front sensor 4F whose detection range is set ahead of the vehicle 10, side sensors 4S whose detection ranges are set to the sides (left and right) of the vehicle 10, and a rear sensor 4R whose detection range is set behind the vehicle 10. The front sensor 4F, the side sensors 4S, and the rear sensor 4R acquire information in the respective detection ranges.

The information acquired by the obtaining device 4 is used to detect objects around the vehicle 10 and/or to detect a traveling lane of the vehicle 10 (the lane in which the vehicle 10 is traveling). The information acquired by the obtaining device 4 is also used to estimate a distance D from the vehicle 10 to the detected object, the type of this object (for example, whether this object is another vehicle or a pedestrian, etc.), and a relative velocity V between the vehicle 10 and this object.

The biological information acquired by the biological sensor 5 is used to detect the abnormality of the driver. The biological sensor 5 is, for example, embedded in a driver's seat 11 on which the driver sits.

Furthermore, the vehicle 10 is provided with a braking device 6 that decelerates the vehicle 10 and an alarming device 7 that outputs alarms to the occupants (including the driver) of the vehicle 10. Specifically, the braking device 6 is a drum brake, a disc brake, or the like, and is provided on wheels 12 of the vehicle 10. The alarming device 7 is configured by, for example, a speaker, a display, an alarming light, or a combination thereof, and is provided in the vicinity of the driver's seat 11. The braking device 6 and the alarming device 7 are both controlled by the control device 1.

The control device 1 is an electronic control device that integrally controls various devices mounted on the vehicle 10, is configured as an LSI device or an embedded electronic device in which a microprocessor, ROM, RAM, etc. are integrated, and is connected to a communication line of an in-vehicle network provided in the vehicle 10. The control device 1 of the present embodiment executes the stop control and the deceleration control.

2. Control Configuration

In general, the collision damage mitigation brake is based on the premise that the driver has no abnormality and also has a risk in the event of erroneous activation, and therefore, the activating situations thereof are limited. However, demands for the deceleration control vary depending on whether or not the abnormality has happened to the driver.

Specifically, when no abnormality has happened to the driver, even if the vehicle 10 is about to collide with some object, there is a high possibility that the driver can avoid the collision by an appropriate driving operation. Therefore, if the driver has no abnormality, it is demanded to execute the deceleration control only in situations with extremely high collision risks and/or for objects with extremely high collision risks to suppress erroneous activation of the deceleration control (to ensure execution accuracy of the deceleration control) and to avoid unnecessary deceleration of the vehicle 10 due to the deceleration control.

On the other hand, when the abnormality has happened to the driver, there is a low possibility that the driver can perform an appropriate driving operation. Therefore, when the driver has the abnormality, it is demanded to execute the deceleration control for situations and/or objects even without extremely high collision risks to more reliably avoid the collision of the vehicle 10.

Thus, in order to more reliably avoid the collision while suppressing unnecessary deceleration of the vehicle 10, it is effective to refer to presence or absence of the abnormality of the driver in determining whether or not to execute the deceleration control. In view of this, the present embodiment is provided with, as an operation mode of the deceleration control, a special mode which is set when the driver has the abnormality. The operation mode is referred to in determining whether or not to execute the deceleration control. For convenience, the operation mode of the normal deceleration control is referred to as a "normal mode" to typographically distinguish it from the special mode described above.

In the stop control, the control device 1 controls the braking device 6 and the alarming device 7 based on the biological information acquired by the biological sensor 5. In the deceleration control, the control device 1 controls the braking device 6 and the alarming device 7 based on various information acquired by the accelerator position sensor 3, the obtaining device 4, and the biological sensor 5. Accordingly, the control device 1 refers to the biological information (presence or absence of the abnormality of the driver) acquired by the biological sensor 5 not only in the stop control but also in the deceleration control. It should be noted that the braking device 6 is controlled in both the stop control and the deceleration control, but the deceleration control has priority over the stop control.

Figure 2:
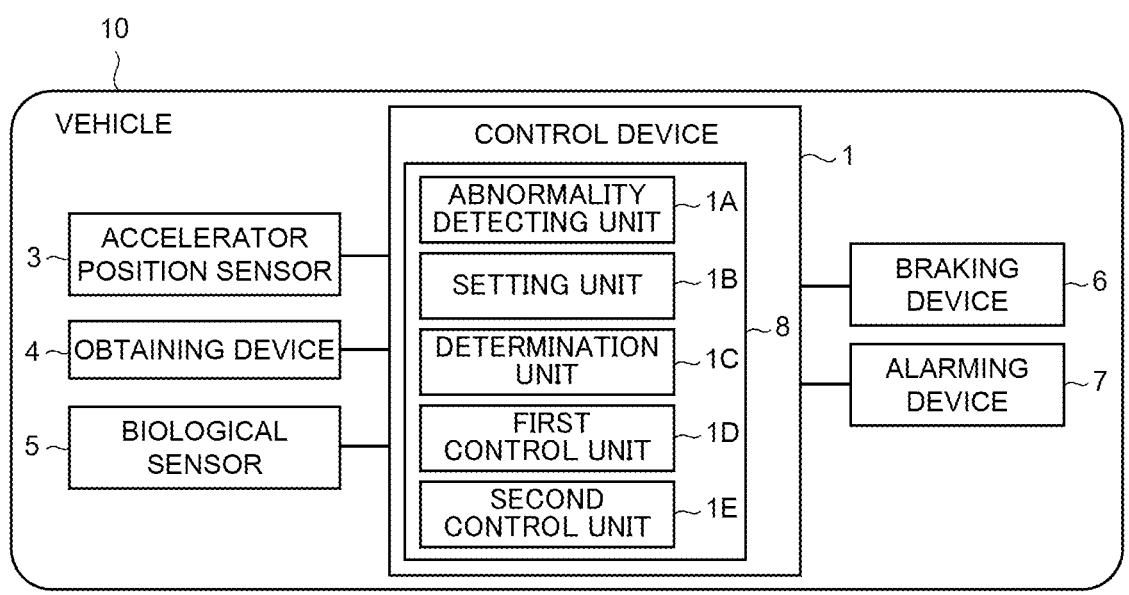
FIG. 2 is a block diagram of the vehicle of FIG. 1.

As illustrated in FIG. 2, the control device 1 includes, as elements for performing the stop control and the deceleration control, an abnormality detecting unit 1A, a setting unit 1B, a determination unit 1C, a first control unit 1D, and a second control unit 1E. The present embodiment illustrates an example in which all of these elements are provided as functions of a computer program (vehicle control program) 8 and the control device 1 executes the computer program 8 to perform the stop control and the deceleration control.

The computer program 8 only needs to be executable by the control device 1, and may be stored in a storage device such as an HDD (Hard Disk Drive) or an SSD (Solid State Drive) in the control device 1, or may be recorded on a medium that can be read by the control device 1 or on an online storage provided on a network to which the control device 1 can be connected, for example.

The abnormality detecting unit 1A detects the abnormality of the driver based on the biological information acquired by the biological sensor 5. The method for detecting the abnormality of the driver is not particularly limited, and various known methods can be used. For example, the abnormality detecting unit 1A may detect the abnormality of the driver when the heart rate acquired by the biological sensor 5 is a predetermined value or less. Incidentally, the abnormality detecting unit 1A may detect the abnormality of the driver based on information acquired by a device other than the biological sensor 5, such as information on the driver's face and/or posture acquired by a camera that captures the driver, information acquired by an operational switch operated by an occupant who noticed the driver's abnormality, and information acquired by an operational switch that the driver with the abnormality operates by oneself.

The setting unit 1B sets the operation mode of the deceleration control based on a detection result of the abnormality detecting unit 1A. Specifically, the setting unit 1B sets the operation mode described above to the normal mode (that is, keeps the normal deceleration control) when the abnormality of the driver is not detected by the abnormality detecting unit 1A, and sets the operation mode described above from the normal mode to the special mode when the abnormality of the driver is detected by the abnormality detecting unit 1A. The setting unit 1B transmits information on the set operation mode to the determination unit 1C and the second control unit 1E as needed.

The determination unit 1C determines whether or not there is the collision risk based on the information acquired by the obtaining device 4, and transmits a determination result to the second control unit 1E as needed. Specifically, the determination unit 1C first identifies a candidate (hereinafter referred to as "target candidate") that will possibly be a target of the collision from the objects existing around the vehicle 10, and then, determines whether there is the collision risk with respect to the identified target candidate.

The determination unit 1C identifies (determines) the object that satisfies a predetermined identifying condition as the target candidate. The identifying condition (condition for the object to be identified as the target candidate) is set looser (easily satisfiable) in the special mode than in the normal mode. This means that the determination unit 1C expands a range for identifying the object around the vehicle 10 as the target candidate in the special mode as compared with the range in the normal mode. That is, the determination unit 1C expands the range of the object that will possibly be the target candidate (loosens the limitation of the target candidate) in the special mode as compared with the range in the normal mode. Accordingly, the determination unit 1C increases an activation sensitivity of the deceleration control in the special mode as compared with that in the normal mode.

The determination unit 1C of the present embodiment executes, as processes for identifying the target candidate, a first process, a second process, and a third process described below. These processes focus on different points. It should be noted that each of the processes uses the identifying condition adapted to be satisfied more easily in the special mode than in the normal mode as described above.

=First Process=

The first process focuses on a detection period T of the object. In the first process, the determination unit 1C refers to the information acquired by the obtaining device 4, compares a period of time (detection period) T for which a single object has been continuously detected around the vehicle 10 with a predetermined period, and identifies the detected object as the target candidate if the detection period T is equal to or longer than the predetermined period.

The predetermined period is set as a first period T1 in the normal mode, and is set as a second period T2 which is shorter than the first period T1 in the special mode. Therefore, the determination unit 1C identifies the object that has been continuously detected for the first period T1 or longer as the target candidate in the normal mode, and identifies the object that has been continuously detected for the second period T2 or longer as the target candidate in the special mode.

The identifying condition in the first process is summarized below for each operation mode.

Normal mode: First period T1 detection period T

Special mode: Second period T2 detection period T (where second period T2<first period T1)

As such, because the second period T2 described above is set shorter than the first period T1, the identifying condition used in the first process is satisfied more easily in the special mode than in the normal mode.

Figure 3:
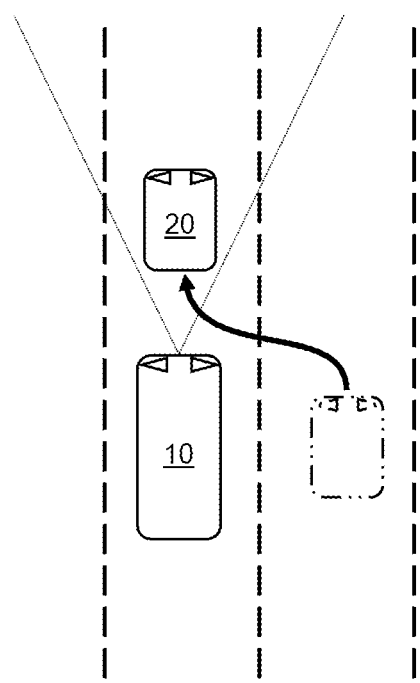
FIG. 3 is a schematic diagram explaining a first process.

As illustrated in FIG. 3, it is assumed that, while the vehicle 10 is traveling, another vehicle 20 suddenly moves ahead of the vehicle 10 in a close distance. In the normal mode, another vehicle 20 is excluded from the target candidate until the detection period T of another vehicle 20 detected by the front sensor 4F becomes the first period T1 or longer. Thus, in the normal mode, the presence or absence of the collision risk with respect to another vehicle 20 is determined after the detection period T has become the first period T1 or longer.

On the other hand, in the special mode, as long as the detection period T of another vehicle 20 detected by the front sensor 4F is the second period T2, which is shorter than the first period T1, or longer, another vehicle 20 is identified as the target candidate. Thus, in the special mode, the presence or absence of the collision risk with respect to another vehicle 20 is determined earlier than that in the normal mode. Therefore, in the special mode, even for a sudden cut-in by another vehicle 20, the deceleration control is executed at an earlier timing.

=Second Process=

The second process focuses on the type of the object. In the second process, the determination unit 1C refers to the information acquired by the obtaining device 4 and estimates the distance D from the vehicle 10 to each object existing around the vehicle 10. Then, in the normal mode, the determination unit 1C further estimates the type of each object and preferentially regards the object of only a predetermined type as the target candidate.

Examples of the object of the predetermined type include a moving object (moving member) such as a pedestrian or another vehicle. In contrast, a stationary object (for example, a guardrail or a sound insulating wall) is set to be less preferential for the target candidate. In general, as compared with moving objects, stationary objects have less reliability in the information acquired by a camera or radar. Therefore, in cases where a stationary object is identified as the target candidate, the accuracy of determining the presence or absence of the collision risk may be lower as compared with cases where a moving object is identified as the target candidate.

In view of this, in the normal mode, the determination unit 1C regards that even if a stationary object is detected, the reliability of the information on this object is low, and prioritizes a moving object over the stationary object in identifying the target candidate. Therefore, in the normal mode, even if a stationary object is in the shortest distance D from the vehicle 10 (even if a stationary object locates the closest to the vehicle 10), since the stationary object is less prioritized as the target candidate, the determination unit 1C identifies the target candidate from moving objects. As such, in the normal mode, the determination unit 1C of the present embodiment identifies the target candidate with priority in the reliability of the information over the distance D from the vehicle 10. The present example preferentially regards the object of the predetermined type as the target candidate by excluding the object of other than the predetermined type (the object having low information reliability) from the target candidate in the normal mode.

On the other hand, in the special mode, the determination unit 1C identifies the target candidate regardless of the type of the object. Therefore, in the special mode, the determination unit 1C identifies the object in the shortest distance D from the vehicle 10 (the object closest to the vehicle 10) as the target candidate, without estimating the type of the object. As such, in the special mode, the determination unit 1C of the present embodiment identifies the target candidate with priority in the distance D from the vehicle 10 over the reliability of the information. Incidentally, the determination unit 1C may exclude objects such as those that are too small for the vehicle 10 to collide with (e.g., dust) or those (ghost objects) that are likely to be erroneously detected by the obtaining device 4 from the target candidate.

The object of the predetermined type, which is preferentially regarded as the target candidate in the normal mode, is not limited to the moving object described above. The reliability of the information acquired by the obtaining device 4 can be estimated based on reflection intensity and depth of radio waves when the obtaining device 4 is a radar and based on, for example, image patterns when the obtaining device 4 is a camera. Therefore, the reliability of the information may be estimated, and an object with the estimated reliability higher than a predetermined value may preferentially be considered as the object of the predetermined type, which is regarded as the target candidate as described above. Alternatively, an object with a structure (shape) that is likely to cause damage in the event of collision may preferentially be considered as the object of the predetermined type, which is regarded as the target candidate as described above.

In the normal mode, the second process of the present embodiment excludes the object within a predetermined range from the target candidate. Specifically, the determination unit 1C in the second process excludes the objects within the detection ranges (predetermined range) of the side sensors 4S and the rear sensor 4R from the target candidate in the normal mode. Therefore, in the normal mode, the determination unit 1C identifies the target candidate from the objects detected based on the information acquired by the front sensor 4F.

On the other hand, in the special mode, the determination unit 1C identifies the target candidate regardless of the detection range of the obtaining device 4. Therefore, in the special mode, the determination unit 1C identifies the target candidate from the objects not only in the detection range of the front sensor 4F but also in the detection ranges of the side sensors 4S and the rear sensor 4R.

The identifying condition in the second process of the present embodiment is summarized below for each operation mode.

Normal mode: Moving in front of the vehicle 10

Special mode: Closest to the vehicle 10

As such, the identifying condition used in the second process is satisfied more easily in the special mode than in the normal mode in a sense that the object of the predetermined type is preferentially regarded as the target candidate in the normal mode, whereas the target candidate is identified regardless of the type of the object in the special mode. In addition, the identifying condition used in the second process is satisfied more easily in the special mode than in the normal mode in a sense that the object within the predetermined range is excluded from the target candidate in the normal mode, but is not excluded in the special mode.

Figure 4:
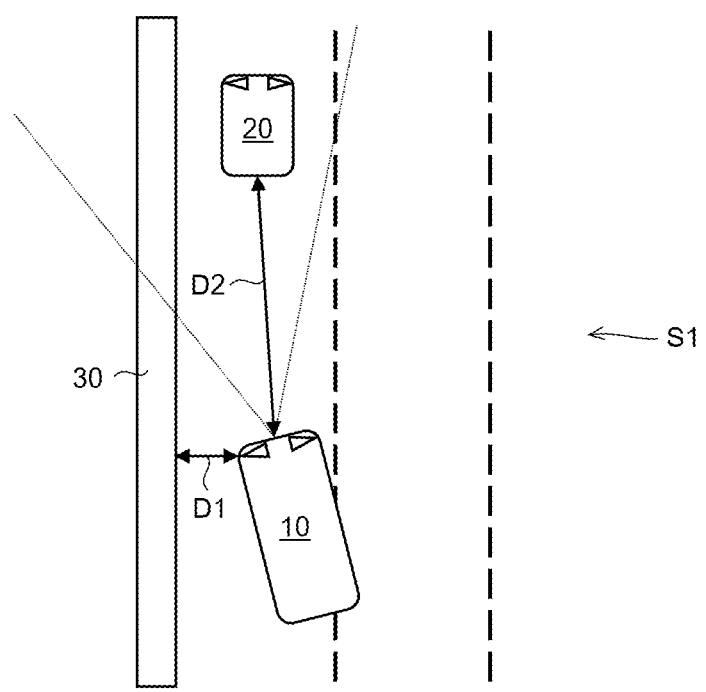
FIG. 4 is a schematic diagram explaining a second process.

As illustrated in FIG. 4, it is assumed that, on a road 51 provided with a guardrail 30, the vehicle 10 is traveling behind another vehicle 20 and a distance D1 from the vehicle 10 to the guardrail 30 is shorter than a distance D2 from the vehicle 10 to another vehicle 20 (D1<D2). In the normal mode, another vehicle 20 which is moving in front of the vehicle 10 may be identified as the target candidate, but the guardrail 30 which is being stationary beside the vehicle 10 is excluded from the target candidate. Therefore, in the normal mode, it is not determined that there is the collision risk with respect to the guardrail 30, and the deceleration control is not executed for the guardrail 30.

On the other hand, in the special mode, the guardrail 30 which locates the closest to the vehicle 10 around the vehicle 10 is identified as the target candidate. Therefore, in the special mode, it is determined whether or not there is the collision risk with respect to the guardrail 30, and if it is determined that there is the collision risk, the deceleration control is executed. As such, in the special mode, the deceleration control may be executed even for a stationary object and an object beside or behind the vehicle 10.

=Third Process=

The third process focuses on the traveling lane of the vehicle 10. In the third process, the determination unit 1C refers to the information acquired by the obtaining device 4 and detects the object existing around the vehicle 10 and the traveling lane of the vehicle 10. Then, in the normal mode, the determination unit 1C excludes the object outside the traveling lane from the target candidate.

On the other hand, in the special mode, the determination unit 1C identifies the target candidate based on the traveling direction of the vehicle 10 regardless of the traveling lane. Specifically, in the special mode, the determination unit 1C identifies the target candidate based on the information acquired by the obtaining device 4 whose detection range is directed to the traveling direction of the vehicle 10, without estimating the traveling lane. For example, when the vehicle 10 is moving forward (when the traveling direction is forward), in the special mode, the determination unit 1C identifies the target candidate from the objects within the detection range of the front sensor 4F. The traveling direction of the vehicle 10 can be estimated by known methods based on, for example, a detection value of a steering angle sensor provided in a steering device.

The identifying condition in the third process is summarized below for each operation mode.

Normal mode: In the traveling lane of the vehicle 10
Special mode: In the traveling direction of the vehicle 10

As such, the identifying condition used in the third process is satisfied more easily in the special mode than in the normal mode in a sense that the object outside the traveling lane is excluded from the target candidate in the normal mode, but is not excluded in the special mode.

As illustrated in FIG. 5(*a*), it is assumed that the vehicle 10 is traveling on a road S2 where the number of lanes is reduced and another vehicle 20 is parked ahead of the end of the traveling lane L (outside the traveling lane L and in front of the vehicle 10). In the normal mode, since another vehicle 20 outside the traveling lane L of the vehicle 10 is excluded from the target candidate, the presence or absence of the collision risk is not determined for another vehicle 20.

On the other hand, in the special mode, another vehicle 20 existing in the traveling direction (here, front) of the vehicle 10 is identified as the target candidate regardless of the traveling lane L of the vehicle 10. Therefore, in the special mode, the presence or absence of the collision risk is determined for another vehicle 20, and if it is determined that there is the collision risk, the deceleration control is executed.

As illustrated in FIG. 5(*b*), it is assumed that the vehicle 10 is traveling on a multi-lane road S3 that curves to the left, and in an adjacent lane Lo to the right of the traveling lane L, another vehicle 20 is traveling ahead of the vehicle 10. In the normal mode, since another vehicle 20 outside the traveling lane L of the vehicle 10 is excluded from the target candidate, the presence or absence of the collision risk is not determined for another vehicle 20.

On the other hand, in the special mode, another vehicle 20 existing in the traveling direction (here, front) of the vehicle 10 is identified as the target candidate regardless of the traveling lane L of the vehicle 10. Therefore, in the special mode, the presence or absence of the collision risk is determined for another vehicle 20, and if it is determined that there is the collision risk, the deceleration control is executed.

As such, in the special mode, even for the object outside the traveling lane L of the vehicle 10, it may be determined that there is the collision risk based on the traveling direction of the vehicle 10.

As described above, after identifying the target candidate, the determination unit 1C determines whether or not there is the collision risk with respect to the identified target candidate. As for this determination method, various known methods can be applied. For example, based on the distance D from the vehicle 10 to the target candidate and the relative velocity V between the vehicle 10 and the target candidate, the determination unit 1C may determine that there is the collision risk at a timing when the braking device 6 needs to start being activated in order to avoid the collision with the target candidate (immediately before the collision with the target candidate becomes unavoidable).

The first control unit 1D executes the stop control when the abnormality of the driver is detected by the abnormality detecting unit 1A. When the abnormality of the driver is detected, the first control unit 1D of the present embodiment first outputs an alarm by controlling the alarming device 7, and after a predetermined abnormality alarm period T3 has elapsed since then, controls the braking device 6 to decelerate the vehicle 10 (starts the stop control), and eventually stops the vehicle 10. In the stop control, the first control unit 1D controls the braking device 6 so that a deceleration of the vehicle 10 does not exceed a predetermined value from a viewpoint of safety.

The second control unit 1E executes the deceleration control when the determination unit 1C determines that there is the collision risk. When it is determined that there is the collision risk, the second control unit 1E of the present embodiment first outputs an alarm by controlling the alarming device 7, and after a predetermined emergency alarm period T4 has elapsed since then, controls the braking device 6 to decelerate the vehicle 10 (starts the deceleration control). The emergency alarm period T4 is set shorter than the abnormality alarm period T3 (T4<T3). As described above, when the abnormality of the driver is detected and it is determined that there is the collision risk, the deceleration control by the second control unit 1E is executed with priority over the stop control.

The second control unit 1E discontinues or ends the deceleration control when at least one of Conditions 1 to 4 described below is satisfied.

Condition 1: The collision risk has disappeared during the alarm and before the start of the deceleration control.

Condition 2: The collision risk has disappeared during the execution of the deceleration control in the normal mode.

Condition 3: A predetermined cancelling condition has been satisfied.

Condition 4: The vehicle 10 has stopped.

The satisfaction or dissatisfaction of Condition 1 is determined based on the determination result of the determination unit 1C. If Condition 1 is satisfied, the second control unit 1E discontinues the deceleration control before the start of the deceleration control. In this case, although the alarm is outputted by the alarming device 7, the deceleration control is not executed.

The satisfaction or dissatisfaction of Condition 2 is determined based on the operation mode set by the setting unit 1B and the determination result of the determination unit 1C. When the determination unit 1C determines that there is no collision risk during the deceleration control in the normal mode (when the determination result of the determination unit 1C is overturned), the second control unit 1E interrupts the deceleration control. On the other hand, during the execution of the deceleration control in the special mode, even if the determination unit 1C determines that there is no collision risk (even if the determination result of the determination unit 1C is overturned), the second control unit 1E continues the deceleration control without interruption.

Condition 3 is provided for the occupant of the vehicle 10 to intentionally discontinue the deceleration control. Similar to the identifying condition, the cancelling condition used in Condition 3 varies depending on the operation mode of the deceleration control. Specifically, the cancelling condition is set to be satisfied less easily in the special mode than in the normal mode.

The cancelling condition of the present embodiment is summarized below for each operation mode.

Normal mode: A predetermined cancel operation has been performed at least once.

Special mode: The predetermined cancel operation has been performed multiple times.

The present embodiment illustrates an example in which the cancel operation described above is a depressing operation to the accelerator pedal 2. The depressing operation to the accelerator pedal 2 is counted once every time the accelerator position AP transmitted from the accelerator position sensor 3 exceeds a predetermined value, for example.

The satisfaction or dissatisfaction of Condition 3 is determined only when the determination unit 1C determines that there is the collision risk. When Condition 3 is satisfied, the second control unit 1E discontinues the deceleration control regardless of whether or not the deceleration control has already been executed. Therefore, if the cancelling condition is satisfied during the alarm and before the start of the deceleration control, the second control unit 1E discontinues the deceleration control without executing the deceleration control, and if the cancelling condition is satisfied during the execution of the deceleration control, the second control unit 1E discontinues the deceleration control that is being executed.

In contrast to Conditions 1 to 3 described above, Condition 4 is an end (completion) condition of the deceleration control. When Condition 4 is satisfied, the collision has been avoided, so that the second control unit 1E ends the deceleration control. The satisfaction or dissatisfaction of Condition 4 may be determined by known methods, for example, based on a detection value of a rotation speed sensor that detects a rotation speed of the wheels 12.

3. Flowchart

Figure 6:
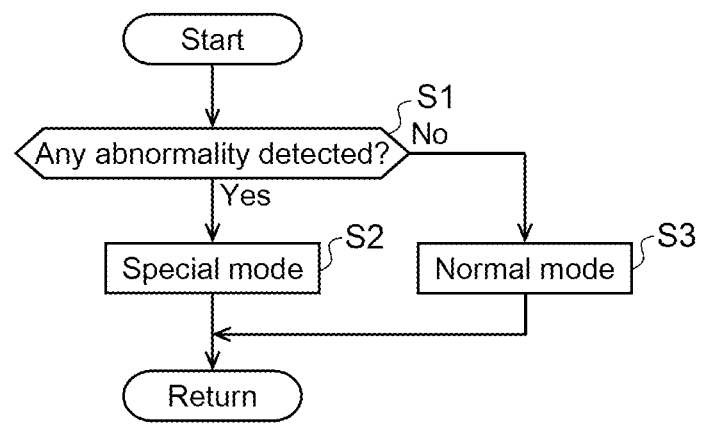
FIG. 6 is a flowchart illustrating a process executed by a setting unit.
Figure 9:
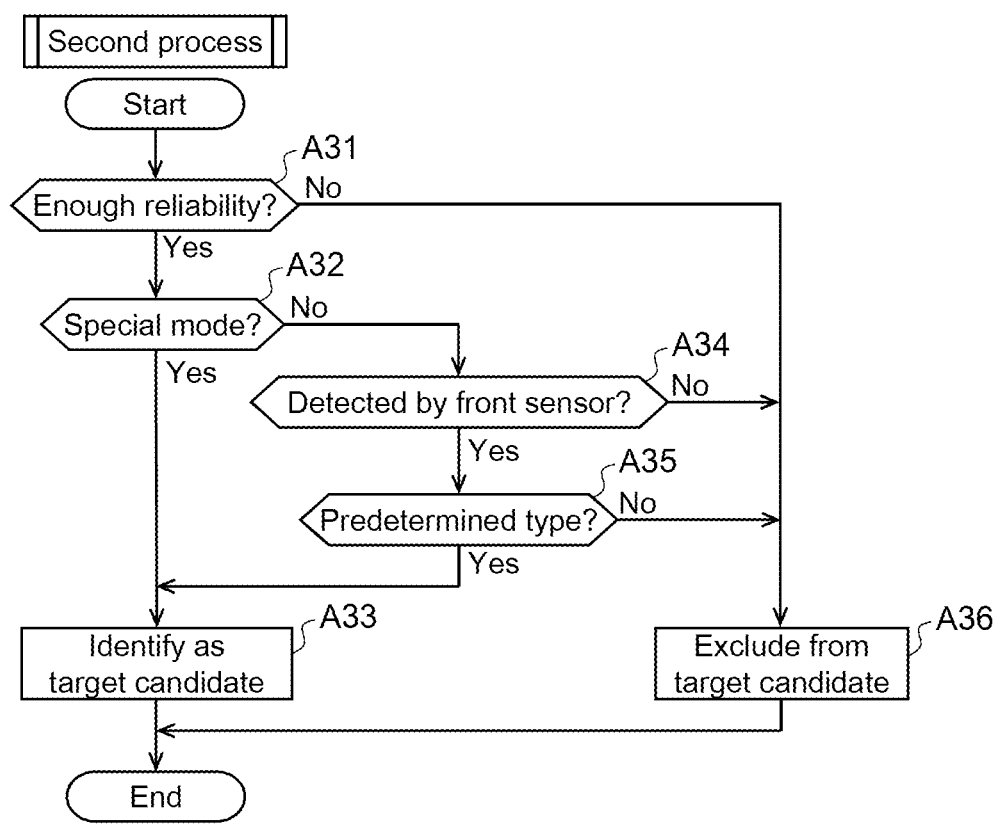
FIG. 9 is a flowchart (subprocess flowchart of FIG. 7) illustrating the second process.
Figure 10:
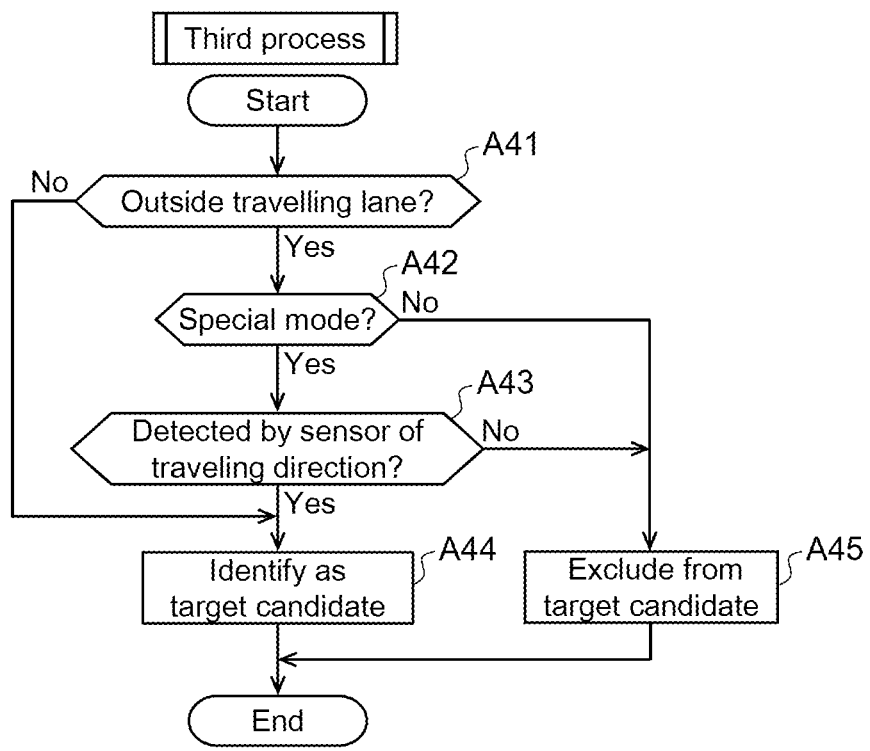
FIG. 10 is a flowchart (subprocess flowchart of FIG. 7) illustrating the third process.
Figure 11:
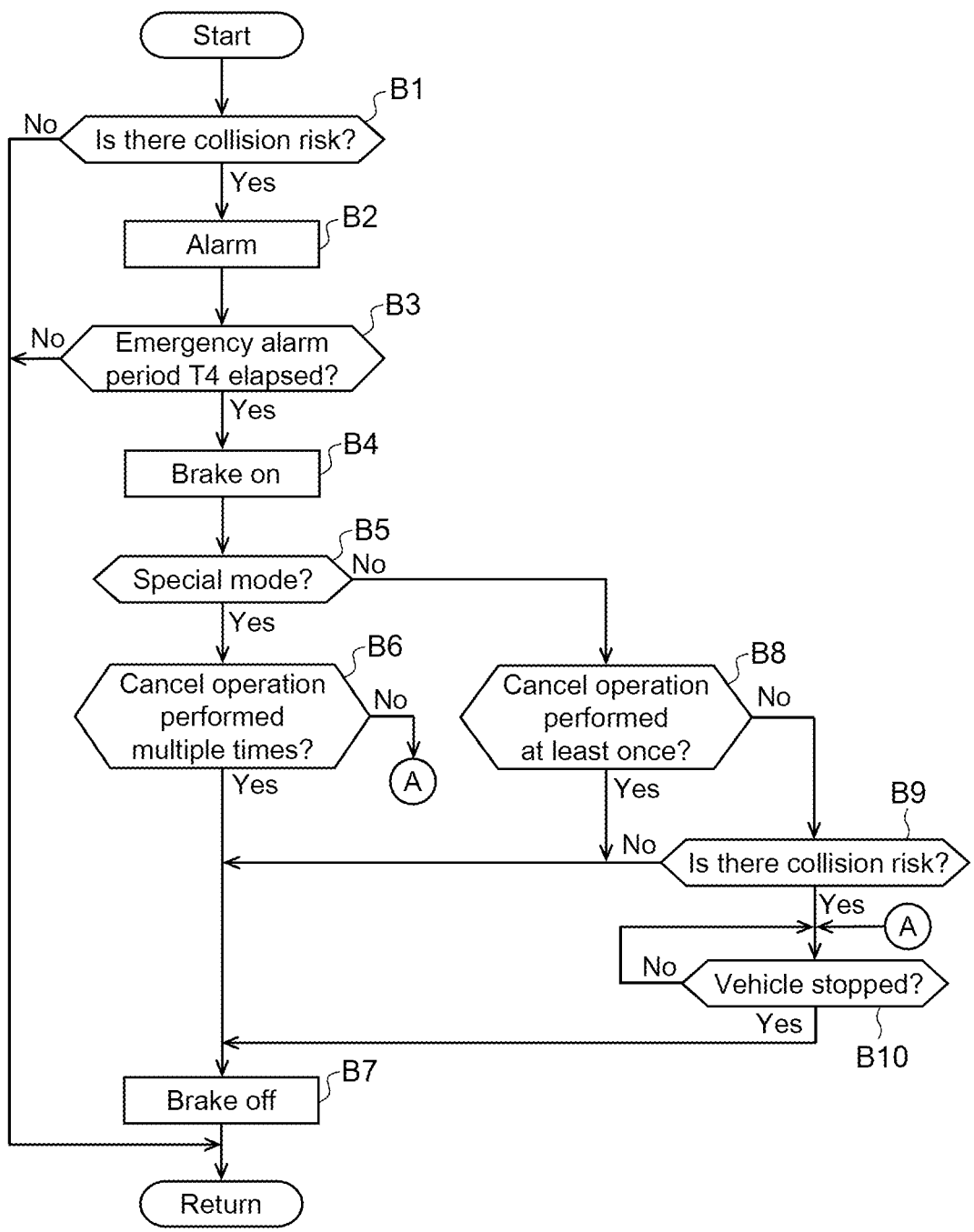
FIG. 11 is a flowchart illustrating a process executed by a second control unit.
Figure 12:
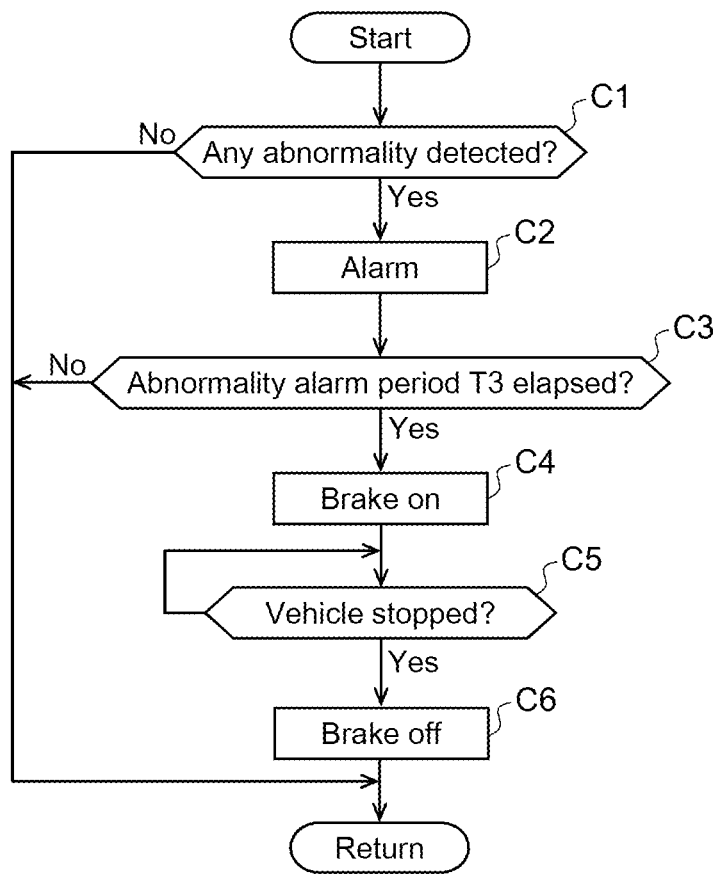
FIG. 12 is a flowchart illustrating a process executed by a first control unit.

FIGS. 6 to 12 are flowcharts illustrating procedures of the control (vehicle control method) performed by the control device 1. Specifically, the flow of FIG. 6 illustrates a process (setting step) performed by the setting unit 1B, and the flows of FIGS. 7 to 10 illustrate a process (determination step) performed by the determination unit 1C. Further, the flow of FIG. 11 illustrates a process (second control step) performed by the second control unit 1E, and the flow of FIG. 12 illustrates a process (first control step) performed by the first control unit 1D.

These flows start when the ignition of the vehicle 10 is turned on and end when the ignition of the vehicle 10 is turned off or when the vehicle 10 is automatically stopped by the stop control. It is assumed that, during the execution of these flows, the information acquired by the accelerator position sensor 3, the obtaining device 4, and the like is transmitted to the control device 1 as needed. Further, it is assumed that the information on the operation mode and on the presence or absence of the collision risk is transmitted and received between the elements 1A, 1B, 1C, and 1D in the control device 1 as needed.

As illustrated in FIG. 6, in the setting unit 1B, it is determined whether or not the abnormality of the driver is detected by the abnormality detecting unit 1A (Step S1). When the abnormality of the driver is detected, the operation mode of the deceleration control is set to the special mode (Step S2), whereas, when the abnormality of the driver is undetected, the operation mode described above is set to the normal mode (Step S3), and the flow returns.

Figure 7:
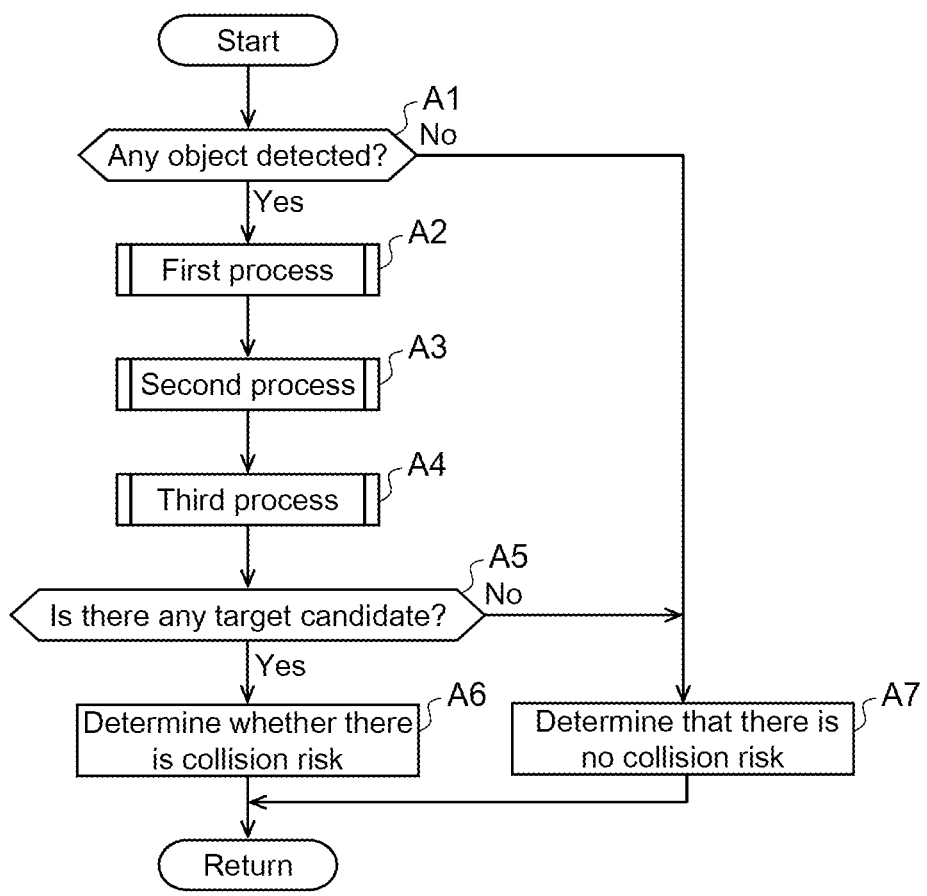
FIG. 7 is a flowchart illustrating a process executed by a determination unit.

As illustrated in FIG. 7, in the determination unit 1C, it is determined whether or not any object is detected by the obtaining device 4 (Step A1). If no object is detected here, it is determined that there is no collision risk (Step A7), and the flow returns. On the other hand, if some object is detected, the first process, the second process, and the third process described above are performed to determine whether or not to identify this object as the target candidate (Steps A2 to A4). The order of the execution of Steps A2 to A4 is not particularly limited, so that each process of Steps A2 to A4 may be performed simultaneously, for example.

Figure 8:
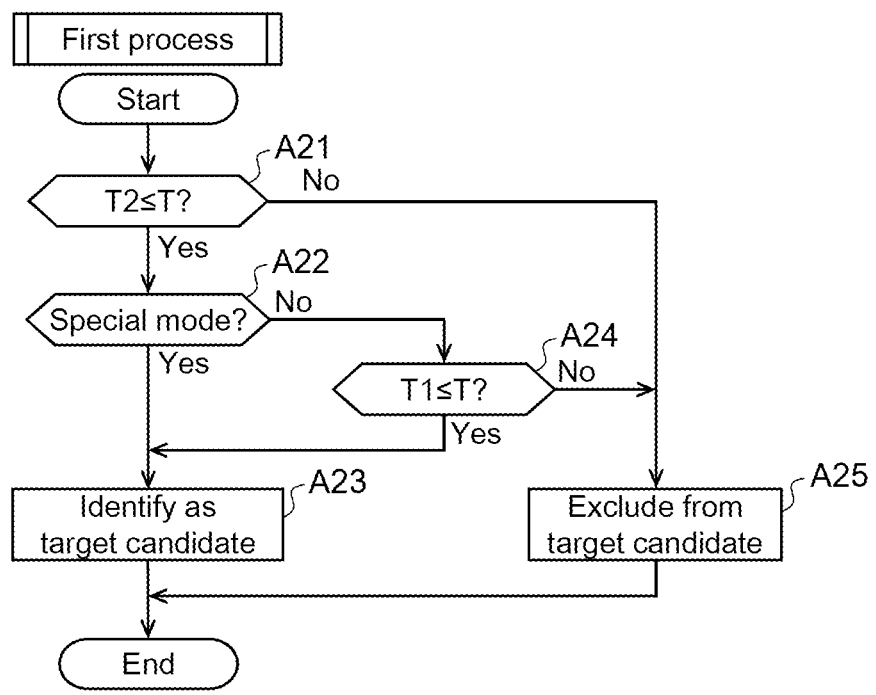
FIG. 8 is a flowchart (subprocess flowchart of FIG. 7) illustrating the first process.

FIGS. 8 to 10 are subprocess flowcharts of FIG. 7.

As illustrated in FIG. 8, in the first process, it is determined whether or not the detection period T of the object is the second period T2 or longer (Step A21). If the detection period T is shorter than the second period T2 here, the object is excluded from the target candidate (Step A25). On the other hand, if the detection period T is the second period T2 or longer, it is determined whether or not the operation mode of the deceleration control is the special mode (Step A22), and if it is the special mode, the detected object is identified as the target candidate (Step A23).

In contrast, when the operation mode of the deceleration control is the normal mode in Step A22, it is determined whether or not the detection period T is the first period T1 (>second period T2) or longer (Step A24). If this determination result is positive, the object is identified as the target candidate (Step A23), and if negative, the object is excluded from the target candidate (Step A25).

As illustrated in FIG. 9, in the second process, it is first determined whether or not the information acquired by the obtaining device 4 has at least a certain level of reliability (Step A31). If it is determined that there is no certain level or more of reliability, the object is excluded from the target candidate (Step A36). On the other hand, when it is determined that there is at least the certain level of reliability, it is determined whether or not the operation mode of the deceleration control is the special mode (Step A32), and if it is the special mode, the object is identified as the target candidate (Step A33).

In contrast, when the operation mode of the deceleration control is the normal mode in Step A32, it is determined whether or not the object is detected by the front sensor 4F (Step A34), and if this determination result is positive, it is determined whether or not the object is the object of the predetermined type (Step A35). If the determination result of Step A35 is also positive, the object is identified as the target candidate (Step A33). On the other hand, if the determination result of either Step A34 or A35 is negative, the object is excluded from the target candidate (Step A36).

As illustrated in FIG. 10, in the third process, it is determined whether or not the object is detected outside the traveling lane of the vehicle 10 (Step A41). If this determination result is negative, the object is identified as the target candidate (Step A44). On the other hand, if the determination result of Step A41 is positive, it is determined whether or not the operation mode of the deceleration control is the special mode (Step A42), and if it is the special mode, it is determined whether or not the object is detected by the obtaining device 4 whose detection range is directed to the traveling direction (Step A43). If the determination result of Step A43 is also positive, the object is identified as the target candidate (Step A44). On the other hand, if the determination result of either Step A42 or A43 is negative, the object is excluded from the target candidate (Step A45).

When all of the first process, the second process, and the third process described above are completed, the process proceeds to Step A5 of the flow of FIG. 7, and it is determined whether or not the target candidate is identified. When the target candidate is identified by at least one of the first process, the second process, and the third process described above, it is determined whether or not there is the collision risk with respect to the identified target candidate (Step A6), and the flow returns. On the other hand, if the target candidate is not identified, it is determined that there is no collision risk (Step A7), and the flow returns.

As illustrated in FIG. 11, in the second control unit 1E, it is confirmed whether or not there is the collision risk (Step B1), and if it is determined that there is no collision risk, the flow returns.

On the other hand, if it is determined that there is the collision risk, the alarming device 7 is controlled to output the alarm (Step B2). After that, the determination of Step B1 is repeated until the emergency alarm period T4 elapses (until the process proceeds to the Yes route from Step B3), and the alarm of Step B2 is continued as long as it is determined that there is the collision risk. Then, the deceleration control is started after the emergency alarm period T4 has elapsed (Step B4). If it is determined that there is no collision risk before the emergency alarm period T4 elapses, Condition 1 described above is satisfied, so that the deceleration control is discontinued and the alarm is stopped.

In Step B4, the braking device 6 is activated to decelerate the vehicle 10. Next, it is determined whether or not the operation mode of the deceleration control is the special mode (Step B5), and if it is the special mode, it is determined whether or not the cancel operation is performed multiple times (Step B6). If this determination result is positive, because the cancelling condition is satisfied, the deceleration control is interrupted. Specifically, the activation of the braking device 6 is canceled (Step B7), and the flow returns.

On the other hand, if the determination result of Step B6 is negative, the process proceeds to Step B10, and the deceleration control is continued until the vehicle 10 stops (until the process proceeds to the YES route from Step B10). Then, when the vehicle 10 is stopped (Condition 4 described above is satisfied), the process of Step B7 is performed and the deceleration control ends.

When the operation mode of the deceleration control is the normal mode in Step B5, it is determined whether the cancel operation is performed at least once (Step B8). If this determination result is positive, because the cancelling condition is satisfied, the deceleration control is interrupted (Step B7). On the other hand, if the determination result of Step B8 is negative, reconfirmation is made on whether or not it is determined that there is the collision risk (Step B9).

If it is determined that there still is the collision risk, the deceleration control is continued until the vehicle 10 stops (until the process proceeds to the YES route from Step B10), and the deceleration control ends after the vehicle 10 is stopped (Step B7). If it is determined in Step B9 that there is no collision risk, because Condition 2 described above is satisfied, the deceleration control is interrupted (Step B7)

As illustrated in FIG. 12, in the first control unit 1D, it is determined whether or not the abnormality of the driver is detected by the abnormality detecting unit 1A (Step C1). If no abnormality of the driver is detected, the flow returns. On the other hand, if the abnormality of the driver is detected, the alarming device 7 is controlled to output the alarm (Step C2).

After that, the determination of Step C1 is repeated until the abnormality alarm period T3 elapses (until the process proceeds to the YES route from Step C3), and the alarm of Step C2 is continued as long as the abnormality of the driver is detected. Then, the stop control is started after the abnormality alarm period T3 has elapsed (Step C4). It should be noted that, if the abnormality of the driver is no longer detected before the abnormality alarm period T3 elapses, the stop control is discontinued.

In Step C4, the braking device 6 is activated to decelerate the vehicle 10. Then, after the vehicle 10 is stopped (after the process proceeds to the YES route from Step C5), the activation of the braking device 6 is canceled (Step C6), and the stop control ends.

4. Actions and Effects

According to the control device 1, the vehicle control method, and the computer program 8 described above, following actions and effects can be obtained.

(1) In the special mode which is set when the abnormality of the driver is detected, the range for identifying the object around the vehicle 10 as the candidate is expanded as compared with the range in the normal mode provided for cases in which the abnormality of the driver is undetected. This results in a higher probability of determining that there is the collision risk with respect to the target candidate in the special mode, so that the opportunity to execute the deceleration control increases. Therefore, when the abnormality happens to the driver, the deceleration control can be executed more reliably. Accordingly, even if the driver is in a state unable to drive, the vehicle 10 can be automatically decelerated by the deceleration control, which can reduce the collision risk more reliably.

On the other hand, when the operation mode of the deceleration control is the normal mode, there is a high possibility that the collision can be avoided by the driver's operation, so that by narrowing the target candidate as compared with that in the special mode, it is possible to reduce the opportunity to determine that there is the collision risk. This reduces erroneous activation of the deceleration control (unnecessary execution of the deceleration control) when there is no abnormality of the driver, so that unnecessary deceleration of the vehicle 10 due to the deceleration control can be suppressed.

(2) As compared with the normal mode, in the special mode, an object with a shorter detection period T is also regarded as the target candidate, so that the target candidate can be identified earlier. As a result, in the special mode, even if the target is detected late, the deceleration control is started at an earlier timing as compared with the timing in the normal mode, which can increase the probability of avoiding the collision of the vehicle 10 by the deceleration control even in the event of a sudden cut-in by another vehicle 20 as illustrated in FIG. 3.

On the other hand, as compared with the special mode, in the normal mode, an object with a longer detection period T is regarded as the target candidate, so that identifying the target candidate by erroneous detection is suppressed. This enhances the accuracy of determining whether or not there is the collision risk, reducing the erroneous activation of the deceleration control. Therefore, unnecessary deceleration of the vehicle 10 due to the deceleration control can be further suppressed.

(3) In the special mode, since the target candidate is identified regardless of the type of the object, the deceleration control can be executed for any types of objects. Accordingly, in the event of the abnormality of the driver, the collision risk can be more reliably reduced for any types of objects.

On the other hand, in the normal mode, the object of the predetermined is preferentially regarded as the target candidate (the object of the predetermined type is regarded as the target candidate with priority over other objects), so that the execution of the deceleration control is avoided for the object such as the one detected based on unreliable information or the one with a structure that is less likely to cause damage even in collision, for example. Therefore, unnecessary deceleration of the vehicle 10 due to deceleration control can be further suppressed.

(4) In the special mode, since the target candidate is identified regardless of whether or not the object is detected within the predetermined range, the deceleration control can be executed for the object located in any directions. As a result, in the event of the abnormality of the driver, the collision risk (for example, not only the risk of a front collision, but also a side collision) can be reduced more reliably for the object located in any directions.

On the other hand, in the normal mode, by excluding the object within the predetermined range from the target candidate (by restricting the target candidate to the object outside the predetermined range), the execution of the deceleration control can be avoided for the object beside or behind the vehicle 10, for example. Therefore, in a situation where the abnormality of the driver is not detected and there is a high possibility that the driver can avoid the collision by steering the vehicle 10, unnecessary deceleration of the vehicle 10 due to the deceleration control can be further suppressed.

(5) In the special mode, since the target candidate is identified based on the traveling direction of the vehicle 10 regardless of the traveling lane of the vehicle 10, even if the driver is in a state unable to steer the vehicle 10, the deceleration control can be executed for the object in the traveling direction. This can more reliably reduce the collision risk also for the object outside the traveling lane in the event of the abnormality of the driver.

Figure 5A:
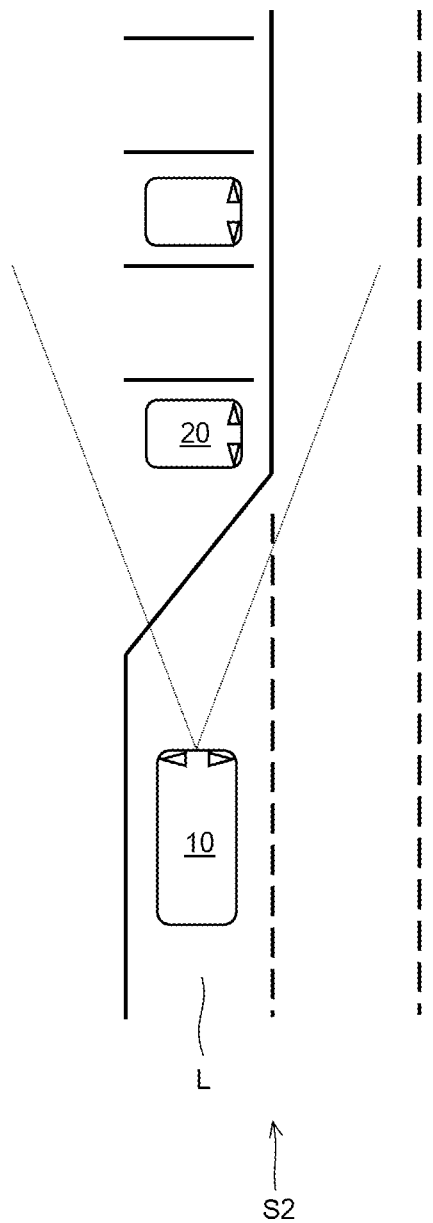
FIGS. 5(a) and 5(b) are schematic diagrams illustrating a third process.
Figure 5B:
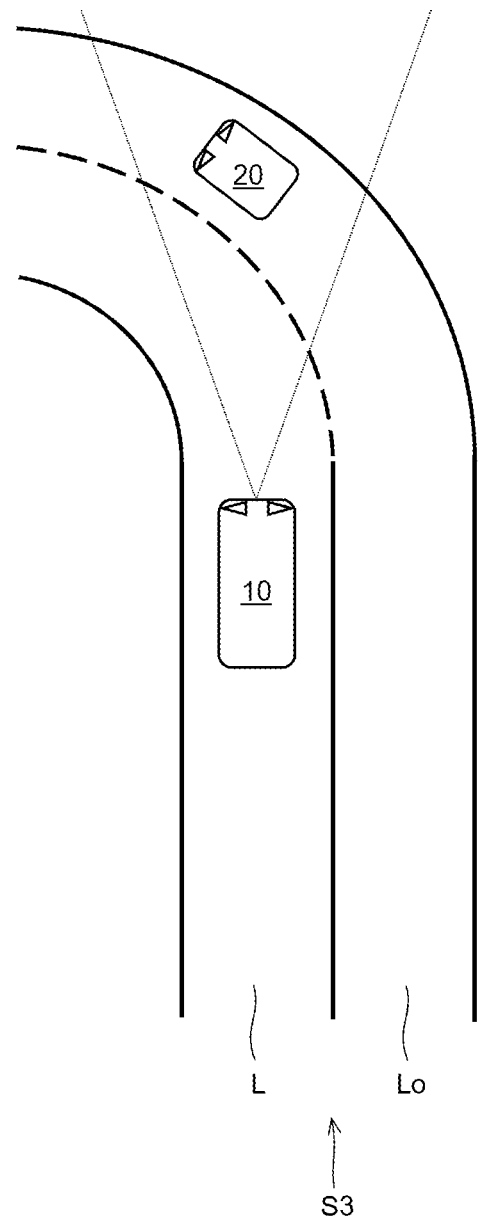

On the other hand, in the normal mode, the object outside the traveling lane of the vehicle 10 is excluded from the target candidate (the target candidate is limited to the object in the traveling lane), so that, on the roads S2 and S3 respectively illustrated in FIGS. 5(a) and 5(b), the execution of the deceleration control for another vehicle 20 can be avoided. Therefore, in a situation where the abnormality of the driver is not detected and there is a high possibility that the driver can avoid the collision by steering the vehicle 10, unnecessary deceleration of the vehicle 10 due to the deceleration control can be further suppressed.

(6) If it is determined that there is no collision risk during the alarm in response to the determination that there is the collision risk and before the start of the deceleration control, the deceleration control is discontinued, so that unnecessary deceleration of the vehicle 10 due to the deceleration control can be further suppressed. However, as described above, in the special mode, since there is a high probability of determining that there is the collision risk as compared with the normal mode, the deceleration control is less likely to be discontinued. Thus, when the abnormality of the driver is detected, even if the driver is in a state unable to drive, the collision risk of the vehicle 10 can be more reliably reduced.

(7) In the special mode, even if it is determined that there is no collision risk, the ongoing deceleration control is continued, so that the collision risk of the vehicle 10 can be more reliably reduced. As such, after the vehicle 10 has started decelerating by the deceleration control in the special mode, because the deceleration control is continued regardless of the presence or absence of the collision risk, the collision risk of the vehicle 10 can be more reliably reduced even if the driver is in a state unable to drive.

On the other hand, in the normal mode, since the executed deceleration control is interrupted when it is determined that there is no collision risk, unnecessary deceleration of the vehicle 10 due to the deceleration control can be further suppressed.

(8) In the normal mode, the deceleration control is discontinued when the cancel operation is performed at least once, whereas in the special mode, the deceleration control is discontinued when the cancel operation is performed multiple times. As such, in the special mode, the deceleration control is less easily discontinued (the cancelling condition for discontinuing the deceleration control is less easily satisfied) than in the normal mode, so that the collision risk of the vehicle 10 can be more reliably reduced.

In the event of the abnormality of the driver, the driver in convulsions, for example, may unintentionally perform the cancel operation. Regarding this, when the number of the cancel operations for discontinuing the deceleration control is set larger in the special mode than in the normal mode as described above, the deceleration control can be inhibited from being discontinued by an unintended cancel operation in the event of the abnormality of the driver.

On the other hand, in the normal mode, since the deceleration control is discontinued even by a single cancel operation, the deceleration control can be easily discontinued when the driver determines that the deceleration control is unnecessary. As a result, unnecessary deceleration of the vehicle 10 due to the deceleration control can be further suppressed.

5. Modifications

The content of the control by the control device 1 described above is an example. The determination unit 1C only needs to expand the range for identifying the object around the vehicle 10 as the target candidate in the special mode as compared with the range in the normal mode, and the identifying method of the target candidate is not limited to the first process, the second process, and the third process described above. In the determination unit 1C, any one of the first process, the second process, and the third process described above may be omitted, or an identifying method other than these processes may alternatively be used.

The second control unit 1E may activate the braking device 6 at multiple levels of strength in the deceleration control. For example, the second control unit 1E may activate the braking device 6 with a relatively weak strength and then with a relatively strong strength.

The conditions for discontinuing or ending the deceleration control are not limited to Conditions 1 to 4 described above. For example, a canceling switch which is operable by the driver may be provided in the interior of the vehicle 10, and the deceleration control may be discontinued or ended when the canceling switch is operated. Similarly, the stop control may be configured to be cancelable in response to an operation on a canceling switch provided in the interior of the vehicle 10.

The specific content of the alarm outputted before the execution of the stop control and the deceleration control is not particularly limited. The contents of the alarm may differ between before the execution of the stop control and before the execution of the deceleration control.

DESCRIPTION OF REFERENCE SYMBOLS

1 control device (vehicle control device)
1A abnormality detecting unit
1B setting unit
1C determination unit
1D first control unit
1E second control unit
2 accelerator pedal
3 accelerator position sensor
4 obtaining device
4F front sensor
4S side sensor
4R rear sensor
5 biological sensor
6 braking device
7 alarming device
8 computer program (vehicle control program)
9 vehicle
10 driver's seat
11 wheel
20 another vehicle
30 guardrail
AP amount of depression (accelerator position)
D distance
D1 distance from vehicle 10 to guardrail 30
D2 distance from vehicle 10 to another vehicle 20
L traveling lane
Lo adjacent lane to right
S1, S2, S3 road
T detection period
T1 first period
T2 second period
T3 abnormality alarm period
T4 emergency alarm period
V relative velocity

The invention claimed is:

1. A vehicle control device, comprising:
a first controller that executes, when an abnormality of a driver of a vehicle is detected, stop control which serves as a driver abnormality response system and which automatically decelerates the vehicle at a predetermined deceleration rate and then stops the vehicle;
a second controller that executes, when the vehicle is determined to have a risk of collision, deceleration control which serves as a collision damage mitigation brake and which automatically decelerates the vehicle;
a determinator that identifies an object around the vehicle as a target candidate of the collision and determines whether or not there is the risk of the collision with the identified target candidate; and
a setter that sets, when the abnormality is detected, an operation mode of the deceleration control to a special mode from a normal mode, the normal mode being provided for cases in which the abnormality is undetected,
wherein, when the abnormality is detected and the vehicle is determined to have the risk of collision, the deceleration control is executed with priority over the stop control, and
wherein, when the operation mode of the deceleration control is in the special mode, the determinator more expands a range for identifying the object around the vehicle as the target candidate of the collision than the range in the normal mode.

2. The vehicle control device according to claim 1, wherein the determinator identifies the object that has been continuously detected for a predetermined first period or longer as the target candidate in the normal mode, and identifies the object that has been continuously detected for a predetermined second period or longer as the target candidate in the special mode, the predetermined second period being shorter than the predetermined first period.

3. The vehicle control device according to claim 1, wherein the determinator preferentially regards the object of a predetermined type as the target candidate in the normal mode, and identifies the target candidate regardless of the predetermined type in the special mode.

4. The vehicle control device according to claim 1, wherein the determinator excludes the object within a predetermined range from the target candidate in the normal mode, and identifies the target candidate regardless of the predetermined range in the special mode.

5. The vehicle control device according to claim 1, wherein the determinator excludes the object outside a traveling lane of the vehicle from the target candidate in the normal mode, and identifies the target candidate based on a traveling direction of the vehicle regardless of the traveling lane in the special mode.

6. The vehicle control device according to claim 1, wherein the second controller interrupts the executed deceleration control when the vehicle is determined to have no risk of the collision in the normal mode, and continues the executed deceleration control even when the vehicle is determined to have no risk of the collision in the special mode.

7. The vehicle control device according to claim 1, wherein the second controller discontinues the deceleration control when a predetermined cancel operation by the driver is performed at least once in the normal mode, and discontinues the deceleration control when the cancel operation is performed a plurality of times in the special mode.

8. A computer-implemented vehicle control method, comprising:
executing stop control which serves as a driver abnormality response system and which automatically decelerates the vehicle at a predetermined deceleration rate and then stops the vehicle when an abnormality of a driver of a vehicle is detected;
executing deceleration control which serves as a collision damage mitigation brake and which automatically decelerates the vehicle when the vehicle is determined to have a risk of collision;

identifying an object around the vehicle as a target candidate of the collision and determining whether or not there is the risk of the collision with the identified target candidate; and setting, when the abnormality is detected, an operation mode of the deceleration control to a special mode from a normal mode, the normal mode being provided for cases in which the abnormality is undetected, wherein, when the abnormality is detected and the vehicle is determined to have the risk of collision, the deceleration control is executed with priority over the stop control, and wherein, when the operation mode of the deceleration control is in the special mode, more expanding a range for identifying the object around the vehicle as the target candidate of the collision than the range in the normal mode.

9. A non-transitory computer-readable recording medium having stored thereon a vehicle control program for causing a computer to execute a process, the process comprising:

executing stop control which serves as a driver abnormality response system and which automatically decelerates the vehicle at a predetermined deceleration rate and then stops the vehicle when an abnormality of a driver of a vehicle is detected;

executing deceleration control which serves as a collision damage mitigation brake and which automatically decelerates the vehicle when the vehicle is determined to have a risk of collision;

identifying an object around the vehicle as a target candidate of the collision and determining whether or not there is the risk of the collision with the identified target candidate; and setting, when the abnormality is detected, an operation mode of the deceleration control to a special mode from a normal mode, the normal mode being provided for cases in which the abnormality is undetected, wherein, when the abnormality is detected and the vehicle is determined to have the risk of collision, the deceleration control is executed with priority over the stop control, and wherein, when the operation mode of the deceleration control is in the special mode, more expanding a range for identifying the object around the vehicle as the target candidate of the collision than the range in the normal mode.

* * * * *